United States Patent [19]

Cullinan

[11] Patent Number: 5,686,468

[45] Date of Patent: Nov. 11, 1997

[54] METHODS OF INHIBITING HIRSUTISM AND ALOPECIA IN WOMEN

[75] Inventor: George J. Cullinan, Trafalgar, Ind.

[73] Assignee: Eli Lilly and Company, Indianapolis, Ind.

[21] Appl. No.: 404,858

[22] Filed: Mar. 15, 1995

Related U.S. Application Data

[62] Division of Ser. No. 171,089, Dec. 21, 1993, Pat. No. 5,574,048.

[51] Int. Cl.$^6$ .................................................. A61K 31/445
[52] U.S. Cl. .................... 514/324; 514/212; 514/317; 514/319; 514/427; 514/443; 514/880
[58] Field of Search ................................. 514/337, 410, 514/324, 880, 317, 319

[56] References Cited

U.S. PATENT DOCUMENTS

| | | | |
|---|---|---|---|
| 4,133,814 | 1/1979 | Jones et al. | 548/525 |
| 4,380,635 | 4/1983 | Peters | 546/202 |
| 4,418,068 | 11/1983 | Jones | 514/337 |
| 4,859,585 | 8/1989 | Sonnenschein | 435/29 |
| 5,075,321 | 12/1991 | Schreiber | 514/317 |

FOREIGN PATENT DOCUMENTS

| | | |
|---|---|---|
| WO93/10113 | 5/1993 | Japan. |
| WO93/1074 | 6/1993 | WIPO. |

OTHER PUBLICATIONS

Archer, C.B. et al., "Alopecia neoplastica responsive to tamoxifene", J. Royal Soc. Med., vol. 83, No. 10, 1990, pp. 647–648.
Neubauer, B. L. et al., "The Prostrate", vol. 23, No. 3, 1993, pp. 245–262.
Draper et al., "Effect of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Bryant et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti-estrogen Raloxifene", Am Soc. Bone & Min. Res., Tampa, Sep. 18–22, 1993.
Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti–Estrogen, Simulates the Effects of Estrogen in Inhibiting Bone Resorption Through Regulating TGFB–3 Expression in Bone;" .Am Soc. for Bone and Min. Res., Tampa, Sep. 18–22, 1993.
Black et al., "Distinct, Structure–Related Profiles of Estrogenic and Anti–Estrogenic Activity in the Tamoxifen and LY117018 Series;" The Endocrine Society, Abstract 1982.
Black et al., "Uterine Bioassay of Tamoxifen, Trioxifene, and New Estrogen Antagonist (LY117018) in Rats and Mice," Life Sciences, 26:1980, 1453–1458.
Black et al., "Differential Interaction of Antiestrogens with Cytosol Estrogen Receptors," Molecular and Cellular Endocrinology, 22:1981, 95–103.
Black et al., "Evidence for Biological Action of the Antiestrogens LY117018 and Tamoxifen by Different Mechanism," Endocrinology 109;1981, 987–989.
Black, L.J. "Biological Actions and Binding Properties of a New Estrogen Antagosist LY117018," In: Homone Antagonists, 129–82, 1982 (M.K. Agarwal ed.) Walter de Gruyter and Co., Berlin New York.
Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

(List continued on next page.)

*Primary Examiner*—Shailendra Kumar
*Attorney, Agent, or Firm*—James J. Sales

[57] ABSTRACT

A method of inhibiting hirsutism or alopecia in women comprising administering to a female human in need of treatment an effective amount of a compound having the formula

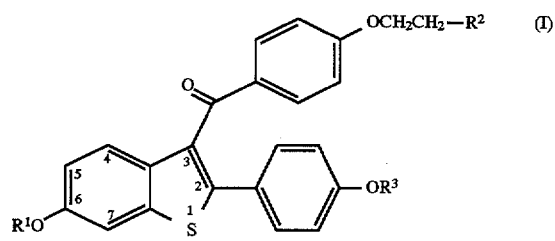

wherein $R^1$ and $R^3$ are independently hydrogen, —CH$_3$,

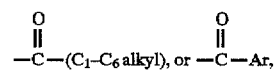

wherein Ar is optionally substituted phenyl;

$R^2$ is selected from the group consisting of pyrrolidine, hexamethyleneamino, and piperidino; or a pharmaceutically acceptable salt of solvate thereof.

4 Claims, No Drawings

OTHER PUBLICATIONS

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl)ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

METHODS OF INHIBITING HIRSUTISM AND ALOPECIA IN WOMEN

This application is a division of application Ser. No. 08/171,089, filed Dec. 21, 1993, now U.S. Pat. No. 5,574,048.

BACKGROUND OF THE INVENTION

Hirsutism (hypertrichosis) is characterized by excessive growth of hair. In women, hirsutism refers specifically to excessive growth of hair in a male pattern and distribution. Clinically, hirsutism in women is seen as a growth of terminal hair on the face (particularly on the upper lip), the chin, chest, back, and lower abdomen (escutcheon). This growth of hair is often seen as unsightly and can be the cause of embarrassment and psychological distress. Hirsutism is a common occurrence at the menopause, but can occur any time after puberty. The etiology of the condition has been linked to over production of androgens by either the ovaries or adrenal glands or both.

Hirsutsim in women can be treated in a variety of ways. Cosmetic treatment of the condition, including shaving, plucking of hairs, and bleaching, while effective in improving the appearance of the patient, are only palliative and must be constantly re-applied. Glucocortacoid steroids are often effective; however, they have the potential of serious side-effects such as Cushing's Syndrome. Oral contraceptives can be effective; however, care must be taken because certain progestins used in common oral contraceptive regiments may actually contribute hirsutism because of their androgenic side-effects. Cimetidine and Spironolactone have shown some effectiveness in the treatment of hirsutism; however, each of these can have unwanted side-effects. Clearly, a more effective and better tolerated agent would be useful.

Alopecia (hair loss) can occur in women for a variety of reasons, and includes female pattern alopecia. Female pattern alopecia is characterized by chronic and progressive hair loss often beginning around thirty years of age and accelerating at menopause. The hair loss is usually confined to thecentral scalp in a diffuse pattern. This loss of hair is cosmetically damaging and often psychologically-disturbing to the patient. The etiology of the condition has been linked to an elevated level of androgens and the subsequent response of androgen sensitive hair follicles. Treatment of the condition is primarily cosmetic in nature, e.g., wigs, hair styles which cover the effected area, etc. The drug, Spironolactone, has been used, but does have side-effects. Clearly, an effective treatment for this condition would be useful.

SUMMARY OF THE INVENTION

This invention provides methods for inhibiting hirsutism or alopecia in women comprising administering to a female human in need of treatment an effective amount of a compound of formula I

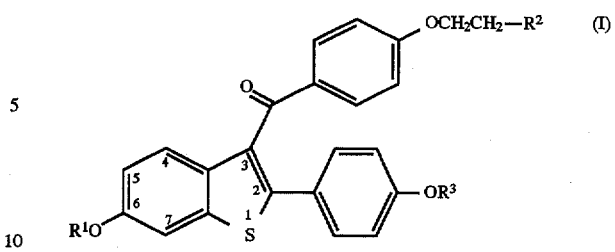

wherein $R^1$ and $R^3$ are independently hydrogen, —CH$_3$,

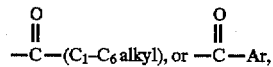

wherein Ar is optionally substituted phenyl;
$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting alopecia or hirsutism in women. The methods of treatment provided by this invention are practiced by administering to a human in need a dose of a compound of formula I or a pharmaceutically acceptable salt or solvate thereof, that is effective to inhibit alopecia or hirsutism. The term inhibit is defined to include its generally accepted meaning which includes prophylactically treating a human subject to incurring a problem described, and holding in check and/or treating an existing problem. As such, the present method includes both medical therapeutic and/or prophylactic treatment, as appropriate.

Raloxifene, a compound of this invention wherein it is the hydrochloride salt of a compound of formula 1, $R^1$ and $R^3$ are hydrogen and $R^2$ is 1-piperidinyl, is a nuclear regulatory molecule. Raloxifene has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, raloxifene activates the same genes as estrogen does and displays the same pharmacology, e.g., osteoporosis, hyperlipidemia. As a result, raloxifene has been referred to as an anti-estrogen with mixed agonist-antagonist properties. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. Substituted phenyl includes phenyl substituted once or twice with $C_1$–$C_6$ alkyl, $C_1$–$C_4$ alkoxy, hydroxy, nitro, chloro, fluoro, or tri (chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit alopecia or hirsutism, according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed to effectively treat the problem.

It is usually preferred to administer a compound of formula I in the form of an acid addition salt, as is customary in the administration of pharmaceuticals bearing a basic group, such as the piperidino ring.

FORMULATIONS

In the formulations which follow, "Active ingredient" means a compound of formula I.

Formulation 1: Gelatin Capsules
Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

| Formulation 2: Raloxifene capsule | |
| --- | --- |
| Ingredient | Quantity (mg/capsule) |
| Raloxifene | 1 |
| Starch, NF | 112 |

| Formulation 2: Raloxifene capsule | |
|---|---|
| Ingredient | Quantity (mg/capsule) |
| Starch flowable powder | 225.3 |
| Silicone fluid 350 centistokes | 1.7 |

| Formulation 3: Raloxifene capsule | |
|---|---|
| Ingredient | Quantity (mg/capsule) |
| Raloxifene | 5 |
| Starch, NF | 108 |
| Starch flowable powder | 225.3 |
| Silicone fluid 350 centistokes | 1.7 |

| Formulation 4: Raloxifene capsule | |
|---|---|
| Ingredient | Quantity (mg/capsule) |
| Raloxifene | 10 |
| Starch, NF | 103 |
| Starch flowable powder | 225.3 |
| Silicone fluid 350 centistokes | 1.7 |

| Formulation 5: Raloxifene capsule | |
|---|---|
| Ingredient | Quantity (mg/capsule) |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

| Formulation 6: Tablets | |
|---|---|
| Ingredient | Quantity (mg/tablet) |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

| Formulation 7: Tablets | |
|---|---|
| Ingredient | Quantity (mg/tablet) |
| Active ingredient | 0.1–1000 |
| Starch | 45 |
| Celulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

| Formulation 8: Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The following compositions are prepared for topical application:

| Formulation 9 | |
|---|---|
| Ingredient | Quantity (mg/5 ml) |
| Hydroxypropylcellulose | 1.5 g |
| Active Ingredient | 1.5–30 g |
| Isopropanol qs | 100 g |

| Formulation 10 | |
|---|---|
| Ingredient | Quantity (mg/5 ml) |
| Hydroxypropylcellulose | 1.5 g |
| Ethyl lactate | 15.0 g |
| Active Ingredient | 1.5–30 g |
| Isopropanol qs | 100 g |

| Formulation 11 | |
|---|---|
| Ingredient | Quantity (mg/5 ml) |
| Hydroxypropylcellulose | 1.0 g |
| Butylated hydroxytoluene | 0.02 g |

7
-continued

Formulation 11

| Ingredient | Quantity (mg/5 ml) |
|---|---|
| Active Ingredient | 1.5–25 g |
| Ethanol qs | 100 g |

Formulation 12

| Ingredient | Quantity (mg/5 ml) |
|---|---|
| Hydroxypropylcellulose | 1.5 g |
| Butylated hydroxytoluene | 0.01 g |
| $C_8$–$C_{12}$ fatty acid triglycerides | 10.0 g |
| Active Ingredient | 1.5–30 g |
| Isopropanol qs | 100 g |

Formulations 9–12 take the form of gels, and are intended for the topical treatment of ache.

Formulation 13

| Ingredient | Quantity (mg/5 ml) |
|---|---|
| Isopropanol | 46.0 g |
| Active Ingredient | 1.0–15 g |
| $C_8$–$C_{12}$ fatty acid triglycerides | 49.0 g |

Formulation 14

| Ingredient | Quantity (mg/5 ml) |
|---|---|
| Ethanol | 69.0 g |
| Ethyl lactate | 10.0 g |
| Active Ingredient | 1.5–20 g |
| $C_8$–$C_{12}$ fatty acid triglycerides | 30.0 g |

Formulation 15

| Ingredient | Quantity (mg/5 ml) |
|---|---|
| Isopropanol | 47.0 g |
| Acetone | 10.0 g |
| Ethyl lactate | 10.0 g |
| Active Ingredient | 1–15 g |
| $C_8$–$C_{12}$ fatty acid triglycerides | 30.0 g |

Formulation 16

| Ingredient | Quantity (mg/5 ml) |
|---|---|
| Ethanol | 95.08 g |
| Butylated hydroxytoluene | 0.02 g |
| Active Ingredient | 1.5–25 g |

8

Formulations 13, 14, 15, and 16 take the form of lotions.

Formulation 17

| Ingredient | Quantity (mg/5 ml) |
|---|---|
| White vaseline | 50.0 g |
| Liquid paraffin | 15.0 g |
| Refined paraffin wax | 32.0 g |
| Active Ingredient | 1–20 g |

Formulation 18

| Ingredient | Quantity (mg/5 ml) |
|---|---|
| White vaseline | 50.0 g |
| Liquid paraffin | 13.0 g |
| Refined paraffin wax | 32.0 g |
| Active Ingredient | 1–20 g |

Formulations 17 and 18 take the form of sticks.

TEST PROCEDURES

HIRSUTISM

Three to twenty women suffering from hirsutism are selected. These patients are initially scored for the extent and severity of hirsutism. The clinical evaluation is made by the methods described in the reference "Methods of Skin Research," John Wiley and Sons, pp 308–318 (1985), and the references cited therein. The patients receive 10–400 mg of an active compound of this invention per day as a single or split dose by oral administration. Alternatively, they apply a 10%, by weight of active ingredient, creme or lotion once or twice a day to the affected areas. The patient continues this protocol for six months. At appropriate intervals, re-evaluation by one of the methods described above would be made.

ALOPECIA

Three to twenty women suffering from female pattern alopecia are selected. These patients are initially scored for the extent and severity of the alopecia. This clinical evaluation is made by the methods described in "Methods of Skin Research," John Wiley and Sons, pp 308–318 (1985) and Habif, T., "Clinical Dermatology," C. V. Mosby Co., Chapter 23, pp 493–504 (1985); and references therein, herein incorporated by reference. Especially helpful in these evaluations is the "hair pluck" procedure and measurement of anagen to telogen ratio. The patients receive 10–400 mg of an active compound of this invention per day as a single or split dose by oral administration. Alternatively, the patients apply a 5–10% (by weight of a compound of this invention) as a creme, lotion, or shampoo to the affected area, once to twice a day. This protocol continues for six months. At appropriate intervals, re-evaluation by one of the methods described in the above references is made. A positive result is exhibited by an increase in the anagen to telogen ratio or an increase in the number of terminal hairs in the affected scalp region.

Utility of the compounds of the invention is illustrated by the positive impact they have on one or more of the symptoms when used in a study as above.

We claim:

1. A method of treating alopecia in a woman comprising administering to a female human in need of treatment an effective amount of a compound having the formula

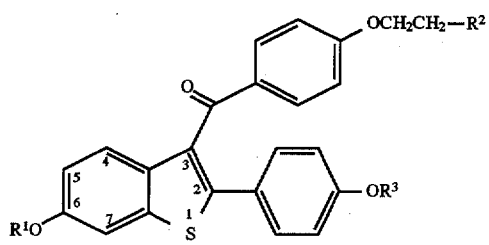

wherein $R^1$ and $R^3$ are independently hydrogen, —$CH_3$,

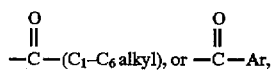

wherein Ar is optionally substituted phenyl;

$R^2$ is piperidino; or a pharmaceutically acceptable salt of solvate thereof.

2. The method of claim 1 wherein said compound is the hydrochloride salt thereof.

3. The method of claim 1 wherein said administration is prophylactic.

4. The method of claim 1 wherein said compound is

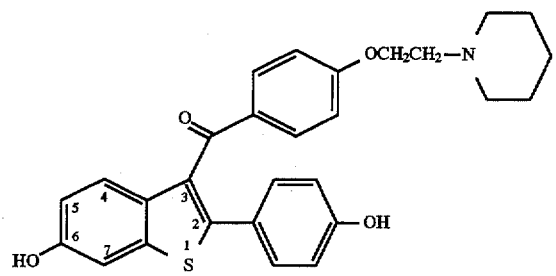

or its hydrochloride salt.